(12) United States Patent
Carlsson et al.

(10) Patent No.: US 7,313,222 B2
(45) Date of Patent: Dec. 25, 2007

(54) METHOD AT A RADIATION THERAPY SYSTEM

(75) Inventors: Per Carlsson, Stockholm (SE); Lars Hedin, Hallstahammar (SE)

(73) Assignee: Elekta AB (publ), Stockholm (SE)

( * ) Notice: Subject to any disclaimer, the term of this patent is extended or adjusted under 35 U.S.C. 154(b) by 179 days.

(21) Appl. No.: 11/159,315

(22) Filed: Jun. 23, 2005

(65) Prior Publication Data

US 2006/0233303 A1   Oct. 19, 2006

(30) Foreign Application Priority Data

Apr. 14, 2005   (SE) .................................... 0500834

(51) Int. Cl.
*A61N 5/10* (2006.01)
(52) U.S. Cl. ......................................... 378/65; 378/205
(58) Field of Classification Search ........ 378/207–209, 378/205, 64–65
See application file for complete search history.

(56) References Cited

U.S. PATENT DOCUMENTS

| | | | |
|---|---|---|---|
| 4,780,898 A | 10/1988 | Sundqvist | |
| 5,107,839 A | 4/1992 | Houdek et al. | |
| 5,528,651 A | 6/1996 | Leksell et al. | |
| 5,553,112 A | 9/1996 | Hardy et al. | |
| 5,727,042 A | 3/1998 | Brenneisen et al. | |
| 5,792,146 A | 8/1998 | Cosman et al. | |
| 6,049,587 A * | 4/2000 | Leksell et al. ................. | 378/65 |
| 6,275,564 B1 | 8/2001 | Ein-Gal | |
| 2002/0085668 A1 * | 7/2002 | Blumhofer et al. ........... | 378/68 |

FOREIGN PATENT DOCUMENTS

WO   98/43552   10/1998

OTHER PUBLICATIONS

Brezovich, Ivan A. et al., "Quality Assurance System to Correct for Errors Arising from Couch Rotation In Linac-Based Stereotactic Radiosurgery", International Journal of Radiation, Oncology Biology Physics, Pergamon Press, vol. 38, No. 4, 1997, pp. 883-890.

* cited by examiner

*Primary Examiner*—Hoon Song
(74) *Attorney, Agent, or Firm*—Buchanan Ingersoll & Rooney PC

(57) ABSTRACT

Calibration of a radiation therapy system comprising a radiation unit with a fixed focus point, a fixation unit for fixing a treatment volume in a patient, and a positioning system. The positioning system comprises a fixed framework, a movable carriage for carrying and moving the entire patient, motor(s), a control system for controlling the motor(s), and at least one engagement point for releasably mounting the fixation unit in fixed engagement with the positioning system. A fixation unit coordinate system defined in relation to the fixation unit is provided. Linearity errors for the motional axes of the carriage and the angular offset between the motional axes and the coordinate system is determined, whereby the relationships between the axes of the coordinate system and the motional axes of the positioning system are determined. The positioning system is then mounted in fixed relationship with the radiation therapy unit and the focus point in relation to the positioning system is determined, whereby the relationship between the focus point and the coordinate system is also determined.

15 Claims, 4 Drawing Sheets

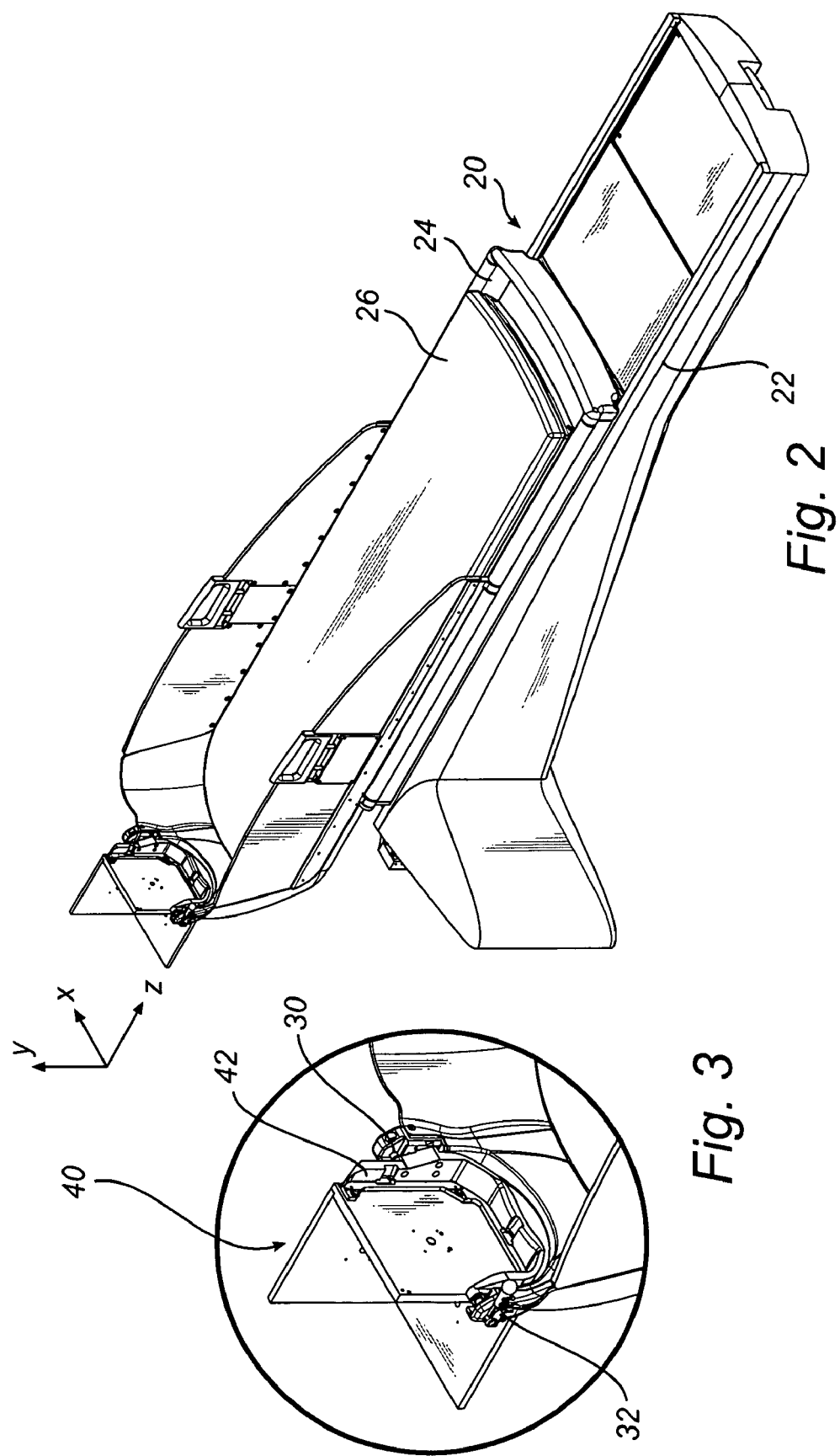

METHOD AT A RADIATION THERAPY SYSTEM

CROSS REFERENCE TO RELATED APPLICATIONS

This application claims the benefit of Swedish Patent Application No. 0500834-7, filed on 14 Apr. 2005.

FIELD OF THE INVENTION

The present invention relates to the field of radiation therapy. In particular, the invention concerns a method of calibrating a positioning system in a radiation therapy system comprising a radiation therapy unit having a fixed radiation focus point.

BACKGROUND OF THE INVENTION

The development of surgical techniques have made great progress over the years. For instance, for patients requiring brain surgery, non-invasive surgery is now available which is afflicted with very little trauma to the patient.

One system for non-invasive surgery is sold under the name of Leksell Gamma Knife®, which provides such surgery by means of gamma radiation. The radiation is emitted from a large number of fixed radioactive sources and are focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all radiation sources intersect or converge, causing the radiation to reach tissue-destructive levels. The point of convergence is hereinafter referred to as the "focus point". Such a gamma radiation device is referred to and described in U.S. Pat. No. 4,780,898.

In the known system, the head of a patient, immobilized in a stereotactic instrument which defines the location of the treatment volume in the head, is secured in a positioning system which moves the stereo-tactic instrument and the head so as to position the treatment volume in coincidence with the focus point. In other words, only the head of the patient is moved when positioning the treatment volume at the focus point. Thus, the size and the weight of the part to be moved, i.e. the head of the patient along with the stereotactic instrument, is well-defined and within a limited range. Motors for providing said movement can be arranged close to or at the stereotactic instrument, and the tolerances of the positioning system may be kept very small. A drawback of the system is that the patient may experience some discomfort when the head is moved while the body is kept still. In particular when the head is moved during the actual surgery, such as is described in U.S. Pat. No. 5,528,651.

Thus, there is a need for a radiation therapy system for brain surgery, in which the entire patient is moved during positioning of the treatment volume at the focus point. However, such a system would need a positioning system capable of accommodating patients of all sizes, ranging from infants to patients exceeding two meters in length and two hundred kilograms in weight. This would require extremely small tolerances for the constructional parts comprised in the patient positioning system in order to achieve sufficient accuracy in the positioning of the treatment volume at the focus point.

Furthermore, due to the fact that the entire patient is moved and not just the head, the motors and the linear guide system provided for movement of the patient would have to be arranged at a greater distance from the focus point, than with the conventional radiation therapy systems. Typically, the larger distances between the motors, the guideways and the focus point enhances the requirement for smaller tolerances even further. Since improved constructional tolerances normally result in increased production costs, especially when producing a system comprising co-operating moving parts, such a positioning system would be very expensive to produce.

SUMMARY OF THE INVENTION

An object of the present invention is to provide an improved method of calibrating a positioning system in a radiation therapy system.

According to a first aspect of the present invention, there is provided a method of calibrating a positioning system in a radiation therapy system comprising a radiation therapy unit having a fixed radiation focus point, a fixation unit for immobilizing a treatment volume in a patient in relation to the fixation unit, and a positioning system for positioning a treatment volume in a patient in relation to said fixed focus point in the radiation therapy unit, the positioning system comprising a fixed framework for rigid engagement with the radiation therapy unit, a movable carriage for carrying and moving the entire patient, at least one motor for providing movement of the carriage along three substantially orthogonal motional axes, a control system for controlling said motor(s), and at least one engagement point for releasably mounting said fixation unit in fixed engagement with the positioning system. The calibration method comprises the steps of providing a fixation unit coordinate system defined in relation to the fixation unit, wherein the fixation unit coordinate system is arranged for defining a treatment volume, determining linearity errors for the motional axes of the carriage and angular offset between said motional axes and said fixation unit coordinate system, whereby the relationships between the axes of said fixation unit coordinate system and the motional axes of the positioning system are determined, mounting the positioning system in fixed relationship with the radiation therapy unit, and determining the radiation focus point of the radiation therapy unit in relation to the patient positioning system, thereby also determining the relationship between said focus point and said fixation unit coordinate system.

Thus, embodiments of the present invention are based on the insight of determining the angular and linear offset between the motional axes of a patient positioning system and a coordinate system defining a treatment volume, and furthermore determining the radiation focus point in relation to the patient positioning system. Accordingly, the position of the focus point in relation to the coordinate system defining the treatment volume is provided via the patient positioning system. Thereby, a correct and accurate positioning of the treatment volume within a patient vis-à-vis the radiation focus point is enabled by using the acquired offset information for compensating, in the movement or positioning of the motional axes of the positioning system during the radiation treatment, for determined angular and linear offsets of the positioning system.

One major advantage resulting from embodiments of the present invention is that the calibration of the motional axes of the patient positioning system can suitably be performed when manufacturing the positioning system, i.e. at the manufacturing plant. Upon assembling the radiation therapy system at the medical facility where the radiation therapy is to be administered, generally a hospital, the actual position of the fixed radiation focus point in relation to the fixation unit coordinate system is measured, and the radiation therapy system is ready for use without the need for subsequent calibration of the positioning system. Thus, embodiments of the invention reduces the need for calibration of the positioning system "on site", which entails several advantages. Since the calibration is made in connection with manufacture of the positioning system, any discrepancies discovered during calibration could easily be attended to without the need for shipping personnel and equipment to a sometimes distant medical facility.

Furthermore, calibration performed in a manufacturing facility enables the use of advanced and precise calibration and measurement tools, which may be difficult or very expensive to ship and possibly unsuitable or even impossible to use at a hospital. An extensive and highly accurate verification of the precision of the calibrated system is enabled if performed in a manufacturing facility, thus providing a better product. It also reduces the amount of work and the space needed during installation of the system at a hospital. The installation personnel do not need to be experts in the calibration of the positioning system. Instead, the installation personnel can focus on the verification of the entire system, i.e. after having mounted the positioning system to the radiation therapy unit.

As used herein, the term fixation unit refers to a unit for fixation of a patient, or rather for a portion of the patient containing a tissue area to be treated. For example, when the treatment area or volume is a portion of tissue within the head of a patient, the fixation unit generally constitutes a head fixation frame which is fixed to the skull of the patient, e.g. by fixation screws or the like. Then, the coordinates of the fixation unit is defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system.

Examples of such a fixation unit and coordinate system includes the Leksell stereotactic head frame and the Leksell XYZ coordinate system, respectively. The Leksell XYZ coordinate system is a Cartesian coordinate system defined by three orthogonal axis perfectly aligned with the frame of a fixation unit, which is arranged with three orthogonal sides. In relation to a patient, the x-axis extends in the medial-lateral direction of the patient, the y-axis extends in the anterior-posterior direction, and the z-axis extends in the cranial-caudal direction. In other words, if a patient is properly positioned in the Leksell XYZ coordinate system, the x-axis would run from ear to ear, the z-axis from head to toe, and the y-axis from back to front of the patient. However, it should be noted that other coordinate systems for defining the volume fixed by the fixation unit, as well as other types of fixation units could be used without departing from the scope of the claimed invention.

The fixation unit for immobilizing a treatment volume is provided with at least one engagement point for mounting the fixation unit in at least one corresponding engagement point provided in the positioning system. When mounted, the fixation unit is in fixed engagement with the patient positioning system and can not be translated or rotated in relation to the positioning system. For this purpose, a plurality of engagement points are preferably used for facilitating the rotational or angular fixation. However, one fixation point locking the angular and translational relationship between the fixation unit and the positioning system is also contemplated within the scope of the invention.

Whether one or several points of engagement between the fixation unit and the patient positioning system are used, the engagement points of the engagement arrangement of the positioning system are manufactured with a very high accuracy without any play or backlash to the fixation frame or other treatment volume fixation unit. This is also the case for the entire fixation unit. In other words, the fixation of the fixation unit to the patient positioning system has a very high positioning accuracy reproducibility, which is higher than that of the entire system. Thereby, the relationship between the fixation unit coordinate system and the engagement points of the fixation unit, and hence of the positioning system, is known by the system and is also fixed. Thus, there is no need for re-calibrating the positioning system whenever a fixation unit is mounted in engagement with the positioning system. Furthermore, several fixation units can be used for the same positioning system without the need for re-calibrating the positioning system for each new fixation unit. Consequently, the fixation unit coordinate system can be calibrated in relation to the positioning system by merely calibrating the engagement points of the positioning system.

Since the fixation unit coordinate system is moved for positioning a fixed radiation focus point at the intended coordinate, the positioning of the fixation unit has to be precisely and accurately controlled. Thus, the positioning system for positioning the fixation unit has to be calibrated such that deviations between the intended positioning in nominal coordinates and the actual positioning in real coordinates, i.e. in relation to the surrounding space, is compensated for. As mentioned above, since the fixation unit coordinate system is fixed in relation to the engagement points of the positioning system, this may be achieved by measuring the movements of the engagement points, thereby determining the linearity errors, such as Abbé errors, and angular offset of the motional axis of the patient positioning system.

According to exemplifying embodiments of the invention, the linearity errors for the motional axes of the carriage in the patient positioning system and any angular offset between the motional axes and the fixation unit coordinate system are determined by measuring the actual position of a measuring point placed in a fix position within the treatment volume or the fixation unit coordination system, which in turn is in fixed relationship with the engagement points. Then, the carriage is moved a nominal distance along one of the three orthogonal axes in order to position the measuring point at a new nominal position, and the difference between the actual position and the nominal position is measured along all three axes and registered. This is repeated along said one axis until all desired positions along the axis have been measured, and is then repeated for the other two motional axes. When this has been performed for all desired positions along all three axes, the control system of the positioning system can use the registered differences for calculating the nominal coordinates required for positioning the fixation unit coordinate system at a desired actual position.

Preferably, for each registered actual position along one axis, the nominal coordinate is stored along with compensation values for all three axes. Since for each measured position along each axis, the difference between actual and nominal position along all three axes are registered, nine compensation values will be stored for each actual position.

It could sometimes be desirable to calibrate each single position within the treatment space, i.e. all coordinates of the radiation fixation coordinate system in which the radiation focus point may be positioned for the radiation therapy. However, according to exemplifying embodiments of the invention, the above described calibration is performed along each coordinate axis of the coordinate system. In other words, when performing the calibration measurement for and along the X-axis, no changes in the nominal positions along the y- and z-axes are made. Furthermore, the measurements along each axis is preferably performed essentially in the centre of the fixation unit coordinate system, i.e. such that the intersection point for the three axes along which calibration measurements are performed is arranged basically in the centre of the coordinate system and accordingly the expected treatment space.

Furthermore, the differences between actual and nominal position is preferably measured for the axis in which the carriage has just performed a nominal movement separate from the measurement of the differences along the other two axes. In other words, the measurement of axis linearity errors is performed in a measurement step which is separate from the measurement step for measuring the straightness of each motional axis. Preferably, the measurement of axis linearity errors is performed for all measured positions prior to performing the straightness measurements, or vice versa. Then, a measurement method and device more suitable for linearity error measurements can be used in one measurement step, and a measurement method and device more suitable for angular offset measurements can be used in the other measurement step.

As understood by the person skilled in the art, the above described embodiment merely provides one suitable example of how the calibration measurements can be performed for determining the linearity errors and angular offsets, and there are numerous other example. For instance, the calibration measurements could be performed using a calibration method simultaneously measuring both linearity errors and angular offsets. Furthermore, the measurements along the orthogonal axes could be performed in arbitrary or random order. Also, in the above described embodiment, the measured position is incremented along one axis at a time. According to other examples, a subsequent measurement position could be reached by incrementing the position along two, or all three, of the orthogonal axes. These examples are all contemplated within the scope of the present invention.

According to exemplifying embodiments of the invention, a calibration measurement adapter is preferably used for the above mentioned calibration of the motional axis of the positioning system. According to one example, the adapter is in the form of an open cube, i.e. a cube having three sides which exactly correspond to and coincide with the orthogonal axes of the fixation unit coordinate system. Then, a dial indicator having a fixed position in real space could for example be used for determining linearity errors of the motional axis. For instance, the abutting end of the dial indicator could be placed in abutment with one of the sides of the cube. When the cube is moved along one of the positioning system axes that ideally should be aligned with one side of the cube, i.e. ideally along one motional axis in the plane, any movements of the dial indicator are registered. Thereby, the differences in the movements of the positioning axis in relation to the ideal movements in the plane of the cube is registered. These indicator movements are of course indicative of movements of the fixation unit coordinate system which are orthogonal to the axis along which the coordinate system is positioned. Thus, the dial indicator is suitable for measuring the angular deviations or offsets between the fixation unit coordinate system and the motional axes of the positioning system In another example, the adapter could be in the form of a fixture, mountable in the engagement points of the positioning system, holding an optical element in the space comprised within the relevant portion of the fixation unit coordinate system. Then, the differential position of the optical instrument for different nominal positions in the coordinate system could be determined using conventional laser interferometer technology, which would be suitable for determining linearity errors, e.g. Abbé errors, in the motional axes of the patient positioning system.

Preferably, one first measurement method for measuring linearity errors are combined with another measurement method for measuring angular offsets, for instance using the above mentioned laser interferometer technology in combination with using a dial indicator in the described manner.

It should also be noted that, even though this is not a preferred embodiment, the fixation unit itself could be used for determining the linearity and angular errors at different positions, providing that a measurement system for accurately measuring the actual position and possibly orientation of the fixation unit is provided.

Of course, and as readily understood by the skilled person, there are many other types of position measurement systems that could be used for determining said linearity errors and angular offsets. Thus, the examples provided herein are not to be seen as limiting the scope of the present invention to such systems. On the contrary, the claimed invention is not restricted to any particular system for determining the actual positions of the engagement points during movement and positioning thereof by the positioning system.

When assembling the radiation therapy system at a treatment site, the fixed framework of the patient positioning system is firmly attached to the radiation therapy unit. Thereby, the position of the radiation focus point, which is fixed in relation to the radiation therapy unit, will also be fixed in relation to the very rigid framework of the patient positioning system. Due to the fixed engagement between the radiation therapy unit and the patient positioning system, any motions of the radiation therapy unit, such as slight vibrations or the like, will result in a corresponding motion of the positioning unit. Thus, once the positioning system has been attached to the radiation therapy unit, there will be no relative movement between the radiation therapy unit, and hence the fixed radiation focus point, and the fixed framework of the positioning system.

Next, the exact position of the fixed radiation focus point in relation to the patient positioning system is determined. As mentioned above, the radiation focus point is defined by the collimators, which are arranged in a collimator arrangement. This can be determined in many different ways. According to one exemplifying embodiment, the radiation unit is provided with reference markings having a known position in relation to the radiation focus point. It should be noted that the term "marking" is intended to be widely interpreted, i.e. including any type of suitable reference marking, such as optical, mechanical, magnetic, inductive, etc. According to one example, the reference marking is in the form of measuring holes provided in the collimator arrangement of the radiation unit.

According to another exemplifying embodiment, a fixture manufactured with high accuracy and fitted with equally high accuracy into the collimator arrangement could be used. The fixture is provided with a mechanical element, such as a recess or a protrusion, denoting the focus point of the collimator arrangement. In further embodiments, the mechanical element could mark a position having a very well defined distance to the focus point.

Then, for both these exemplifying embodiments, a measurement device may be mounted to the patient positioning system, preferably in fixed relationship to the engagement points used for mounting the fixation unit. Thus, the measurement device is used for determining the position of the denoted radiation focus point, or the reference marking. The measurement device could preferably be in the form of a touch sensitive measurement probe, but could as an example also be in the form of an optical measurement device, or the like. The advantage of such a system for determining the accurate position of the radiation focus point is that the radiation focus point could be determined with the radiation shut off, or before the radiation sources have even been loaded into the radiation unit. This of course sets high demands on the accuracy in the positional relationship between the reference marking or point and the radiation focus point.

According to yet another exemplifying embodiment, the fixed radiation focus point is determined by radiation measurements, e.g. using a phantom with radiation sensitive film provided in a certain position within the phantom. Preferably, a phantom for detecting radiation at a small point is used, which is moved around in the radiation area in order to determine the extension and position of the radiation focus point. According to another example, photographic film which is sensitive to gamma radiation could be used. Another method of determining the exact focus position in relation to the positioning system involves the use of a radioactivity sensitive diode having a very well defined sensitive volume. Suitably, a diode providing an output that is linearly proportional to the detected radiation is used. One example of such a such a radiation detecting diode is a semiconductor field detector in the form of a silicon p-n junction diode could be used, which is a conventional arrangement for measuring radiation in order to calibrate a radiation focus point in a medical device. Thus, by scanning the focus area with the diode, the exact relative position of the radiation focus point can be determined. The advantages of such measurements are of course that the position of the radiation focus point is measured directly, as compared to the above described indirect methods of determining the radiation focus point position.

As readily understood by the person skilled in the art, various known methods for determining the radiation focus point could be used, of which some have been described above. However, the present invention is not restricted to the particular examples shown and described herein, but any suitable measurement method for determining the radiation focus point is contemplated within the scope of the present invention.

BRIEF DESCRIPTION OF THE DRAWINGS

Exemplifying embodiments of the invention will now be described in greater detail with reference to the accompanying drawings, in which

FIG. 2 illustrates the positioning system used in the calibration method of the present invention;

FIG. 3 illustrates one example of an adapter for use in determining the linearity errors and angular offset of the motional axes of patient positioning system;

DESCRIPTION OF EXEMPLIFYING EMBODIMENTS

Figure 1:
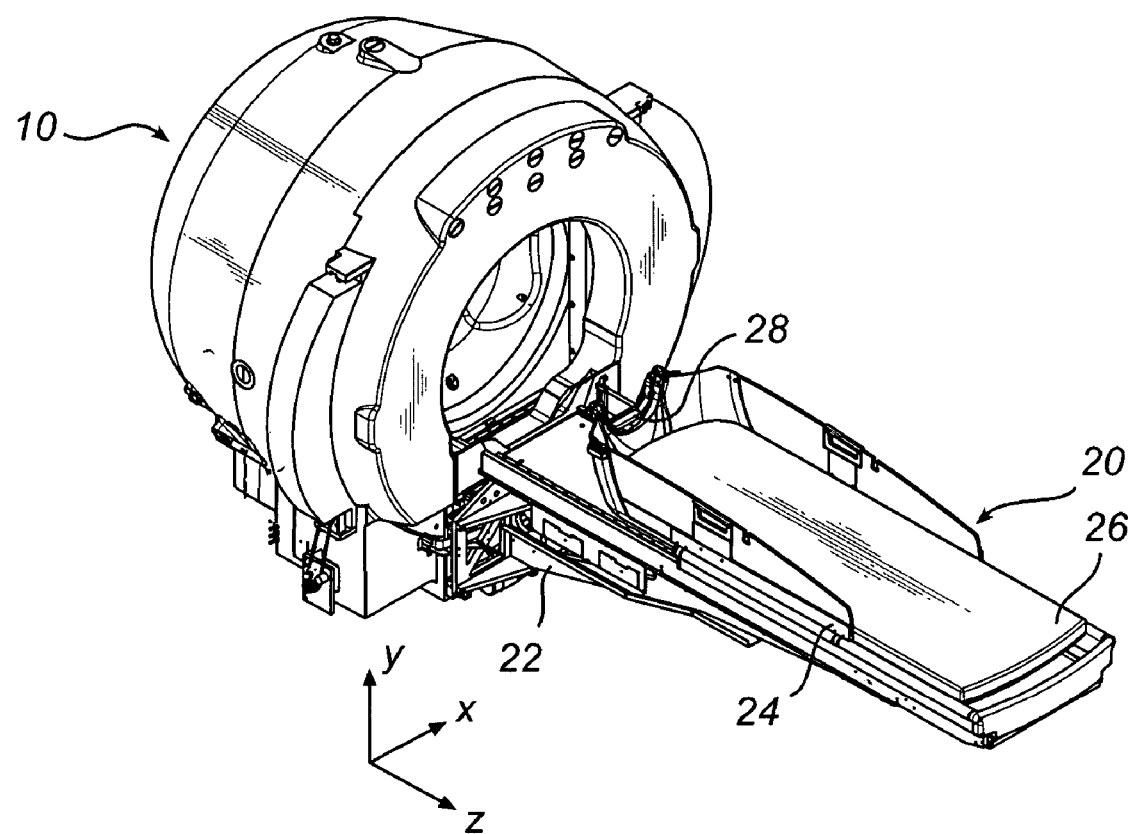
FIG. 1 illustrates the general principle of a radiation therapy system suitable for calibration using the present invention.

With reference to FIGS. 1-6, a radiation therapy system for which the present invention is applicable comprises a radiation unit 10 and a patient positioning unit 20. In the radiation unit 10, there are provided radioactive sources, radioactive source holders, a collimator body, and external shielding elements. The collimator body comprises a large number of collimator channels directed towards a common focus point, in a manner as is commonly known in the art.

The collimator body also acts as a radiation shield preventing radiation from reaching the patient other than through the collimator channels. Examples of collimator arrangements in radiation therapy systems applicable to the present invention can be found in WO 2004/06269 A1, which is hereby incorporated by reference. However, the present invention is also applicable to radiation therapy systems using other arrangements for collimating radiation into a fixed focus point, such as is disclosed in U.S. Pat. No. 4,780,898.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit 50, either directly or via an adapter unit 42. According to the illustrated embodiment, the fixation arrangement 28 comprises two engagement points 30, 32, which are arranged for preventing the patient fixation unit from translational or rotational movement in relation to the movable carriage 24.

As can be understood from FIGS. 1 and 2, the described embodiment concerns a radiation therapy system for providing gamma radiation therapy to a target volume in the head of human patient. Such therapy is often referred to as stereotactic surgery. During therapy, the patient head is fixed in a fixation unit in the form of a stereotactic head frame 50, shown in FIG. 5, which comprises engagement points 51 adapted for engagement with the engagement points 30, 32 of the radiation therapy system. Thus, during the stereotactic surgery, the head of the patient is fixed in the stereotactic frame 50, which in turn is fixedly attached to the patient positioning system via the engagement points 30, 32, 51. During movement of the treatment volume in the head of the patient in relation to the radiation focus point, along the three orthogonal axes x, y, and z shown in FIG. 1, the entire patient is moved along the axes. Thus, there is no relative movement between the head frame 50 and the carriage 24 of the patient positioning system 20.

Figure 5:
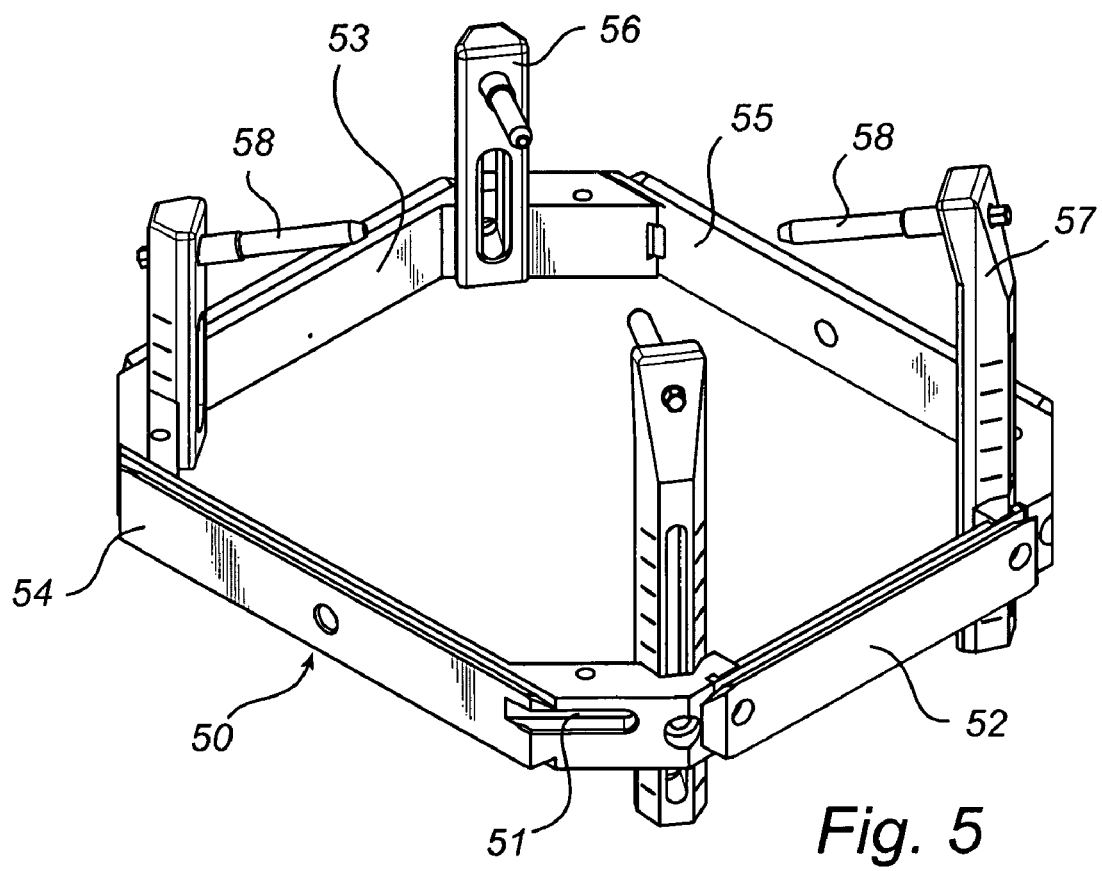
FIG. 5 illustrates a fixation unit.

Turning now to FIG. 5, there is shown a fixation unit in the form of a stereotactic head frame 50. The head frame 50 comprises a base constituted by a forward beam 52, a rear beam 53, and right and left side beams 54, 55. The beams of the base are mounted orthogonally in relation to each other, and the longitudinal extension of each beam are arranged perfectly in parallel with the x- and y-axis directions of the Leksell XYZ coordinate system, which will be described below, where the front and rear beams 52, 53 are parallel to the x-axis, and the side beams 54, 55 are parallel to the y-axis. The beams are provided with engagement points 51 which are arranged for fixed engagement with the engagement points 30, 32 of the fixation arrangement 28.

Furthermore, at each corner of the base there is provided a vertical post 56, 57 which are arranged to hold the screws for fixation of the head in relation to the stereotactic head frame 50 during the whole treatment procedure. Thus, each post 56, 57 is at its upper end provided with a fixation screw 58 for fixation of the head frame to the skull of a patient. Furthermore, the position of each post along the z-axis can be adjusted in adaptation to the size and shape of the head of the patient.

Figure 6:
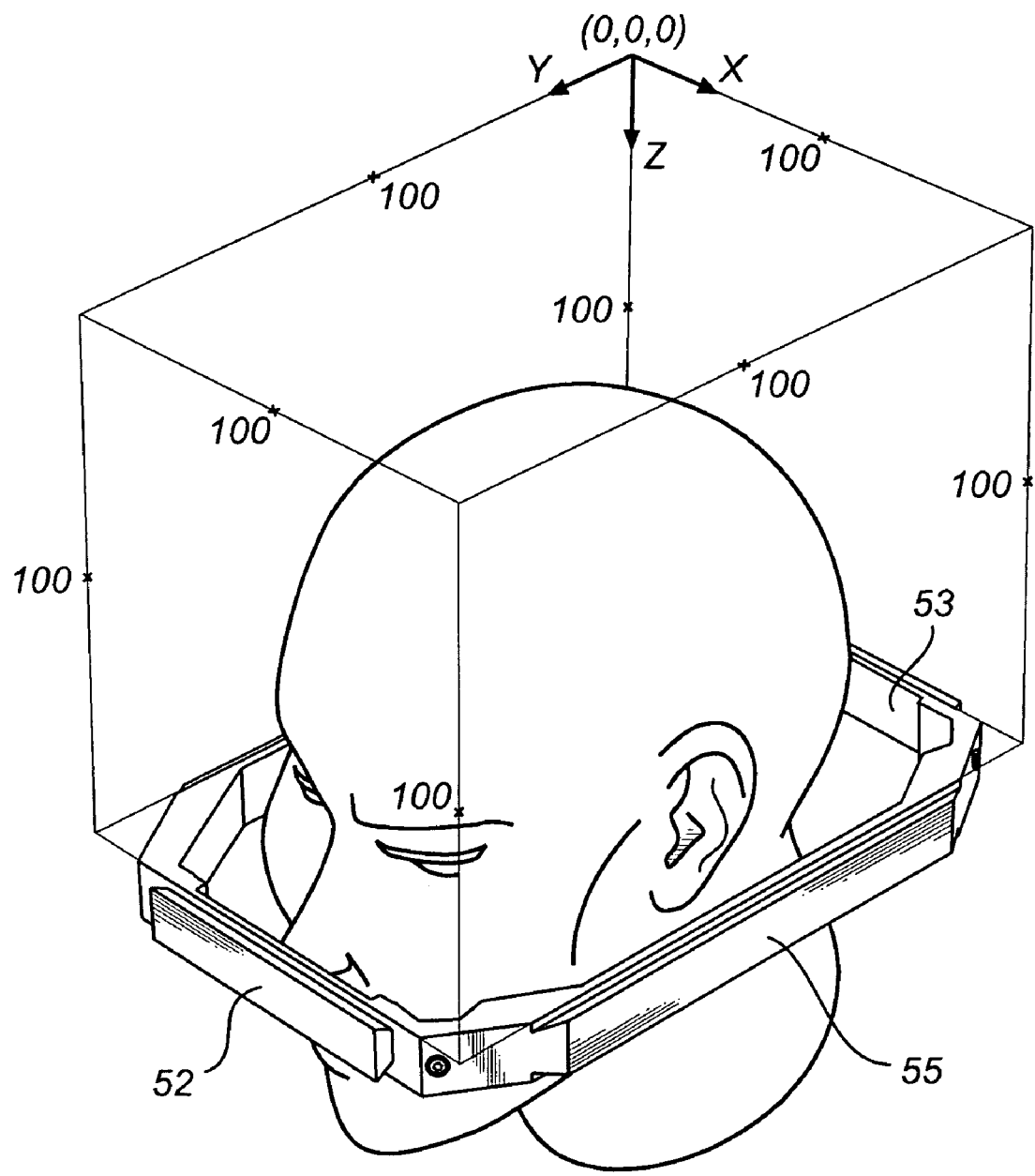
FIG. 6 illustrates the Leksell XYZ coordinate system.

FIG. 6 illustrates the Leksell XYZ coordinate system, which is a Cartesian coordinate system, in connection with a standard frame being applied around the patient head. As can be seen in the figure, the origin of coordinates (0, 0, 0) is located behind the back of the head, outside the right ear and over the top of the head. Thus, any target area or focus in the head of a patient will be defined by positive coordinates. The x-axis extends in parallel to an imaginary line extending from the right ear to the left ear of the patient. The y-axis extends in parallel to a line drawn from the neck (posterior) to the nose (anterior) of the patient. The z-axis extends in parallel to the longitudinal direction of the patient's body. In the following, the coordinates of the Leksell XYZ coordinate system will be referred to as Leksell coordinates.

Returning now to FIGS. 2-4, there is shown an adapter unit 42 fixedly mounted in the engagement points 30, 32 of the fixation arrangement 28. As mentioned above, the adapter unit 42 could be used for facilitated mounting of the stereotactic frame 50. In these figures, however, the adapter unit 42 is used for mounting a calibration reference unit 40 to the fixation arrangement 28 of the positioning unit 20. The reference unit 40 is in the form of an open cube, that is a cube 40 having three orthogonal side walls 44, 46, 48. The extensions of the walls 44, 46, 48 correspond to the Leksell XYZ coordinate system, such that the left side wall 44 lies in the YZ plane, the back side wall 46 lies in the XZ plane, and the bottom side wall 48 lies in the XY plane. The terms "left", "back", and "bottom" are in relation to a patient lying on the bed 26.

Figure 4:
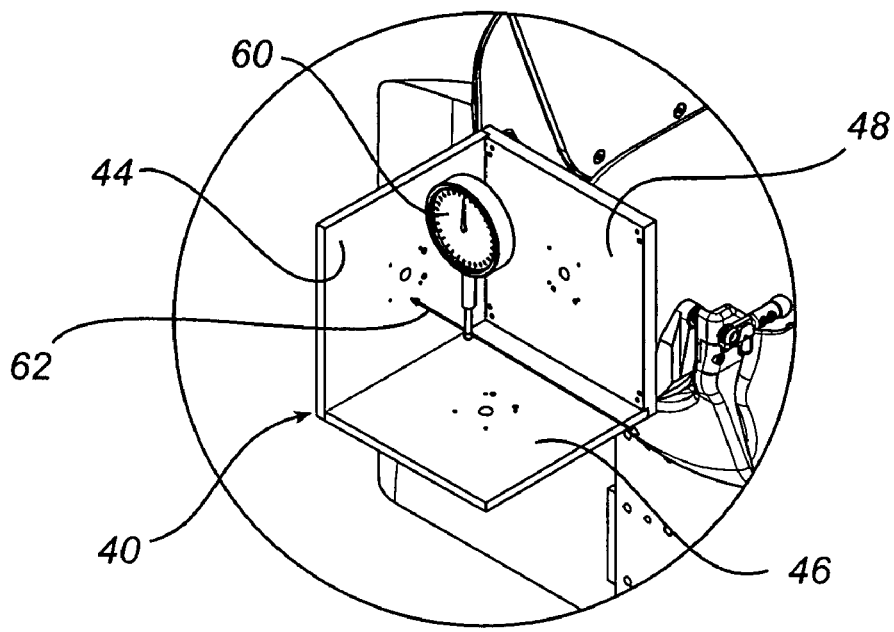
FIG. 4 illustrates the adapter of FIG. 3 during measurement using a dial indicator.

In the described embodiment, two dial indicators 60 are used for performing the calibration measurements. However, for illustrative purposes only one dial indicator is shown in FIG. 4. Each dial indicator 60 comprises a measuring stick or pin 62 and an indicating dial. The movements of the measuring stick 62 in the longitudinal direction thereof is transferred to and displayed by the indicating dial. Thus, when the side wall 44 has a movement in the X-direction, for instance when moving the cube 40 along the y- or z-axis for calibrating angular deviations or offsets thereof, this movement is adopted by the measuring stick 62 and can be registered.

During the calibration operation, the two dial indicators are arranged such that their measuring sticks 62 abut two of the side walls when angular offset measurements are performed for the axis extending in both planes. In other words, when the motional axis providing movements of the Leksell coordinate system along the z-axis is calibrated, the measuring stick of the first and second dial indicator, respectively, abuts the side wall 44 in the YZ plane and the side wall 46 in the XZ plane. Thus, the dial indicator abutting the XZ plane measures angular offsets along the x-axis and the dial indicator abutting the YZ plane, as is shown in the figure, measures angular offsets along the y-axis, when the positioning system moves the cube along the z-axis.

It should be noted that the dial indicators 60 are held in a fixed and accurately defined position, in the vicinity of where the focus point will be positioned in relation to the positioning system, by a holding arrangement, which for illustrative purposes is not shown in FIG. 4. Instead of presenting the result on a dial, the indicators could be connected to electronic storage device for electronically registering and storing the measurement results of the calibration.

According to one embodiment of the invention, the step of measuring for angular offset and the step of measuring for linearity or Abbé errors are performed separately. In the described example, the measurement for angular offset is performed before the measurement for linearity errors, but the order of measurement could just as well be reversed.

When calibrating for angular offset, one motional axis at a time is measured in the manner described above. First, a virtual radiation focus point is defined. The exact position of this virtual focus point is not critical, but the position thereof is fixed throughout the measurements. Thereafter, the positioning system is controlled to position the cube, or the Leksell XYZ coordinate system, for instance such that the virtual focus point is positioned at (0, 100, 100) as described in millimeters in Leksell coordinates. At this point, the measuring sticks 62 of the two dial indicators are in abutment with the back and bottom side walls 46, 48, i.e. the walls in the XZ and the XY plane, respectively. The deflection of the dials are read and the respective reading is registered. Then, the cube, i.e. the coordinate system, is moved along the x-axis in order to position the focus point at (20, 100, 100) in Leksell coordinates. Once again, the dials are read and the reading registered for the new coordinate.

This is repeated along the part of the x-axis which is to be calibrated, e.g. until the virtual focus point is positioned at (200, 100, 100). Then, the virtual focus point is positioned at one end of one of the remaining motional axes, in this example at (100, 0, 100) in Leksell coordinates. Accordingly, the y-axis is now to be calibrated. The dial indicators are repositioned such that the measuring sticks thereof abut the left and bottom side walls 44, 48, and the measurement procedure is repeated for the y-axis. Finally, the virtual focus point is placed at (100, 100, 0), the indicating dials are repositioned and similar measurements are performed for the remaining axis, in this case the z-axis.

The now determined angular offset for each point along the x-, y-, and z-axis, respectively, are stored. Thus, for each point along each axis, there are two compensation values, one for each of the other two axes. These are added together such that for each Leksell coordinate, there is now a compensation value in the x-, y-, and z-direction. Continuing with the calibration method, we now have compensation values intended for the compensation of angular offsets between the Leksell coordinate system and the motional axes of the positioning system. However, this does not take into account possible errors in the linearity of the motional axes, for instance Abbé errors. According to the described embodiment, a second calibration step is used for calibrating the linearity of the motional axes.

Then, a laser interferometer system is used. A first optical element in the form of a reflector is positioned and mounted in fixed relationship with the engagement points 30, 32, for instance using the adapter unit 42, and hence the Leksell coordinate system. A second optical element is located in a fixed position in relation to the fixed framework of the positioning system, i.e. in a fixed position in actual coordinates. Furthermore, a laser is used for measuring changes in the distance between the two optical elements.

First, the Leksell coordinate system is moved such that the virtual focus point is at (0, 100, 100). Then, the virtual focus point is positioned at a new coordinate along the x-axis, whereby the first optical element is moved a nominal distance. The actual moved distance is measured using the laser and compared to the nominal distance that the optical element has been moved, that is as controlled and registered by the positioning system. The difference between the actual and the nominal movements is stored in a calibration table and denotes the linear compensation value for that coordinate. This is then repeated, first along the entire x-axis, and then in similar manner for the y-axis and the z-axis. The differences between nominal positions or movements and actual positions or movements are registered for each measured coordinate. The thus registered values are the compensation values for the x-, y-, and z-axis, respectively.

The compensation values for the linearity errors can then be added to the compensation values for the angular offset. Thus, for each Leksell coordinate, the added compensation value are comprised by nine different compensation values, one linearity compensation and two angular compensations for each axis. Thus, the compensation between actual coordinates and nominal coordinates for each coordinate could be expressed as:

$$(X,Y,Z)=(X_{Nom}+X_{Comp},\ Y_{Nom}+Y_{Comp},\ Z_{Nom}+Z_{Comp})$$

where $$X_{comp}=(\text{LinErr}_{X\text{-}axis}+\text{AngOff}_{Y\text{-}axis}+\text{AngOff}_{Z\text{-}axis})$$

$$Y_{comp}=(\text{AngOff}_{X\text{-}axis}+\text{LinErr}_{Y\text{-}axis}+\text{AngOff}_{Z\text{-}axis})$$

$$Z_{comp}=(\text{AngOff}_{X\text{-}axis}+\text{AngOff}_{Y\text{-}axis}+\text{LinErr}_{Z\text{-}axis})$$

According to an exemplifying embodiment of the invention, the above described calibration steps are performed at the factory where the patient positioning system is manufactured or at least assembled. Following said calibration, the patient positioning system 20 and the radiation unit 10 are rigidly attached to each other, for example by bolting the rigid framework 22 of the patient positioning system 20 to a corresponding rigid framework of the radiation unit 10. This attachment is performed at the medical facility at which the radiation therapy system is intended to be used.

When the patient positioning system 20 and the radiation unit 10 have been rigidly attached to each other at the treatment site, the actual position of the fixed radiation focus point in relation to the patient positioning system is determined. As mentioned above, it is the collimators, i.e. the orientation, design and direction of the collimators together with the sources, comprised in the collimator arrangement of the radiation unit 10 that determines where the radiation focus point will be located. Thus, the actual position of the radiation focus point can be determined and calculated without the need for detecting or measuring the radiation from the radioactive sources.

According to exemplifying embodiments, the determination of the radiation focus point is performed by fitting a fixture with very high accuracy into the collimator arrangement. The fixture is arranged such that the focus point of the collimator arrangement, when the fixture is fitted into the collimator arrangement, is denoted by a discernible recess provided on the fixture. A probe mounted in the engagement points 30, 32 of the patient positioning system is used for discerning the recess and thereby determining the position of the radiation focus point in relation to the positioning system.

Then, when the actual position of the fixed radiation focus point in relation to the positioning system has been determined, the offset between the actual position of the radiation focus point and the assumed position of the virtual focus point is registered and stored. The offset, in coordinates taking into account all three orthogonal axes, is used for compensating between the nominal and actual positional relationship between the radiation focus point and the Leksell XYZ coordinate system.

Even though the present invention has been described above using exemplifying embodiments thereof, alterations, modifications, and combinations thereof, as understood by those skilled in the art, may be made without departing from the scope of the invention as defined in the accompanying claims. For example, the determination of the radiation focus point could be performed by measuring the focus point using a radiation sensitive measurement arrangement, such as a phantom including a photographic film which is sensitive to gamma radiation, or a radiation sensitive diode which could be moved in the treatment volume to detect the radiation focus point. Furthermore, a number of different measurement methods could be used for performing the steps of calibrating the motional axes of the positioning system for linearity errors and angular offsets.

What is claimed is:

1. A method of calibrating a positioning system in a radiation therapy system, the system comprising
   a radiation therapy unit having a fixed radiation focus point;
   a fixation unit for immobilizing a treatment volume in a patient in relation to the fixation unit; and
   a positioning system for positioning a treatment volume in a patient in relation to said fixed focus point in the radiation therapy unit, the positioning system comprising a fixed framework for rigid engagement with the radiation therapy unit, a movable carriage for carrying and moving the entire patient, at least one motor for providing movement of the carriage along three substantially orthogonal motional axes, a control system for controlling said motor(s), and at least one engagement point for releasably mounting said fixation unit in fixed engagement with the positioning system;
   the method comprising the steps of:
   a) providing a fixation unit coordinate system defined in relation to the fixation unit, said fixation unit coordinate system being arranged for defining a treatment volume;
   b) determining linearity errors for the motional axes of the carriage and angular offset between said motional axes and said fixation unit coordinate system, whereby the relationships between the axes of said fixation unit coordinate system and the motional axes of the positioning system are determined;
   c) mounting the positioning system in fixed relationship with the radiation therapy unit; and
   d) determining the radiation focus point of the radiation therapy unit in relation to the patient positioning system, thereby also determining the relationship between said focus point and said fixation unit coordinate system,
   e) storing the information related to the determined focus point as calibration information for enabling an accurate positioning of a treatment volume in relation to the focus point.

2. The method as claimed in claim 1, wherein said step b) of determining linearity errors and angular offset further comprises the steps of
   b1) measuring the actual position of a measuring point, said measuring point being fixed in relation to said engagement point(s);
   b2) moving the carriage a nominal distance along one of the three motional axes of the positioning system to a new nominal position;
   b3) measuring the difference between the actual position and the nominal position of the measuring point along all three axes;
   b4) repeating steps b2) and b3) until all desired positions along said one axis have been measured;
   b5) repeating steps b2) through b4) for the other two motional axes;
   b6) registering said differences along all three axes for a measured position; and
   b7) repeating step b6) for all measured positions;
   such that the control system can use said registered differences for calculating the nominal movements of the carriage that are required to reach an actual position.

3. The method as claimed in claim 2, wherein for each actual position along one axis, a nominal value is registered together with compensation values for all three axes, whereby for each measured position, nine compensation values are stored, three for each axis.

4. The method as claimed in claim 2, wherein the step b3) of measuring the difference comprises measuring the difference for the axis along which the carriage has just moved in a first measurement step, providing an axis linearity measurement, and along the other two axes in a second measurement step, providing an axis straightness measurement, of arbitrary order.

5. The method as claimed in claim 4, wherein said first measurement is performed for all measured positions prior to performing said second measurement, or vice versa.

6. The method as claimed in claim 4, wherein said first measurement is performed using dial indicator measurements.

7. The method as claimed in claim 4, wherein said second measurement is performed using laser interferometer measurements.

8. The method as claimed in claim 2, wherein said step b) of determining linearity errors and angular offset further comprises the steps of mounting a measurement fixture using said engagement point(s) in the positioning system, and fixing said measurement point in said measurement fixture.

9. The method as claimed in claim 1, wherein said step d) of determining the radiation focus point of the radiation therapy unit in relation to the patient positioning system further comprises the steps of:

mounting a fixture unit in fixed relationship with a collimator arrangement arranged for defining said fixed focus point, said fixture unit being provided with a marking denoting the fixed focus point when said fixture unit is mounted in said collimator arrangement, mounting a measurement unit in fixed relationship with the patient positioning system, and measuring the position of said marking using said measurement unit.

10. The method as claimed in claim 9, wherein said measurement unit is mounted in fixed relationship using said engagement point(s).

11. The method as claimed in claim 9, wherein said measurement unit comprises a measurement probe.

12. The method as claimed in claim 1, wherein said step d) of determining the radiation focus point of the radiation therapy unit in relation to the patient positioning system further comprises the steps of:

arranging a radiation measurement arrangement in fixed relationship with the patient positioning system, measuring the radiation emitted in the radiation unit, and determining the radiation focus point in relation to the patient positioning system.

13. The method as claimed in claim 12, wherein said measurement arrangement comprises a radiation sensitive diode.

14. The method as claimed in claim 1, wherein said step d) of determining the radiation focus point of the radiation therapy unit in relation to the patient positioning system is performed at the medical facility where the radiation therapy is to be delivered.

15. The method as claimed in claim 10, wherein said measurement unit comprises a measurement probe.

* * * * *